United States Patent
Berner

Patent Number: 5,267,178
Date of Patent: Nov. 30, 1993

[54] PHOTOMETRIC PROCESS AND COMPUTER CONTROLLED PHOTOMETER

[75] Inventor: Markus Berner, Niederhasli, Switzerland

[73] Assignee: Gretag Aktiengesellschaft, Regensdorf, Switzerland

[21] Appl. No.: 912,705

[22] Filed: Jul. 13, 1992

[30] Foreign Application Priority Data

Jul. 19, 1991 [DE] Fed. Rep. of Germany ..... 91810585

[51] Int. Cl.$^5$ .............................................. G06F 15/42
[52] U.S. Cl. ..................... 364/498; 364/496; 235/462
[58] Field of Search .................. 364/496–498, 364/413.02; 219/10.55 E; 356/328; 235/462

[56] References Cited

U.S. PATENT DOCUMENTS

| | | | |
|---|---|---|---|
| 4,093,991 | 6/1978 | Christie et al. | 364/498 X |
| 4,509,859 | 4/1985 | Markart et al. | 356/446 |
| 4,591,978 | 5/1986 | Peterson et al. | 364/200 |
| 4,703,437 | 10/1987 | Nishimura | 364/498 |
| 4,929,084 | 5/1990 | Mast et al. | 356/328 X |
| 4,935,875 | 6/1990 | Shah et al. | 364/497 |
| 4,961,646 | 10/1990 | Schrammli et al. | 356/328 |
| 4,968,140 | 11/1990 | Berner et al. | 356/328 X |
| 5,147,068 | 9/1992 | Wright | 219/10.55 EX |
| 5,153,827 | 10/1992 | Coutré et al. | 364/413.02 |

FOREIGN PATENT DOCUMENTS 0383322  8/1990  European Pat. Off. .
3627378  2/1988  Fed. Rep. of Germany .

*Primary Examiner*—Kevin J. Teska
*Attorney, Agent, or Firm*—Burns, Doane, Swecker & Mathis

[57] ABSTRACT

A computer controlled spectrophotometer is equipped with a serial interface to which a bar code reader can be connected. Using the bar code reader, calibration and configuration data or functional commands for the spectrophotometer may be read from a data carrier and transmitted to the computer in the spectrophotometer.

16 Claims, 5 Drawing Sheets

33010000

20

1603000000

24

3A0163004842D9645A42BA98A5422D a)

FFB642E5CCBA42DD65AD423CCDD142 b)

20FFE9429999EB422BCCE542E0CBE7 c)

425F9AD942EDCBDA42D298D742B299 d)

D1422067D74261CDD04239FFCF4263 e)

00C842539AC042789ABF422067B142 f)

9CFFB3424B33B3429365AF426C9AA6 g)

42BD66A742AD00A042EA65A042DF98 h)

A442099A9C4220678B4201338F425B i)

999442246876425DCC8B42 j)

PHOTOMETRIC PROCESS AND COMPUTER CONTROLLED PHOTOMETER

BACKGROUND OF THE INVENTION

The invention relates to a photometric process using a corresponding computer controlled spectrophotometer.

A computer controlled photometer of the type involved here is, for example, the portable spectrophotometer SPM 100 of the Gretag AG, Regensdorf, Switzerland, which is in worldwide use. This spectrophotometer supports a plurality of measuring modes (color densities, spectra, colorimetrics, etc.), makes possible measurements under different conditions (standards for color densities, types of light, observer angles for colorimetrics) and also permits free programming of these conditions (for example, types of light). It is further capable of setting and storing several reference and calibrating values.

The operation of the instrument, i.e., the choice of the different measuring modes and conditions and the setting and storage of the different reference and calibration values, etc. is normally carried out manually using the operating keyboard of the instrument. Additionally, a serial interface is provided for the connection of an external computer, through which the instrument may be alternatively controlled by the transmission of the corresponding control data.

As the above-mentioned photometer is a portable, relatively small, manual instrument, the memory and operating possibilities are naturally subject to certain limitations, which in particular often appear to make the entry of complex data via the keyboard cumbersome.

SUMMARY OF THE INVENTION

The foregoing difficulty is to be overcome by the invention, and the operator friendliness of a photometer in accordance with exemplary embodiments of the invention is improved, while simultaneously creating an ability to provide expanded application and functional diversity for the instrument.

These and other objects are attained by a photometric process and photometer according to the invention. Exemplary preferred embodiments and especially advantageous configurations of the process and photometer are described.

A fundamental feature of the invention involves entering the settings or memory space intensive data that are relatively cumbersome to enter manually via the keyboard into an external memory, and to load it from there into the instrument, as needed. Such data includes measuring configurations, measuring modes, measuring conditions, reference and calibration values and the like. The external memory storage may be effected in any manner desired (for example in a ROM or EPROM). Preferably, storage is on a data carrier in a machine readable form, in particular in the form of an optically readable bar code. The control data stored in this manner can then, on the one hand, be read very simply using an inexpensive, commercial bar code reader (wand) and loaded into the photometer, and on the other hand, can be very simply and inexpensively recorded and transported. If, according to an advantageous embodiment of the invention, a printer with graphic capabilities is connected with the photometer and its internal computer is suitably programmed, the prevailing control data and also measuring data, may be printed out as bar codes or the like and thus stored on paper. At a later time, the data may be read in with a reading device and the old configurations, etc. may be easily reconstituted.

Features according to the invention make it possible to carry out complex operations in a highly convenient manner which could only be previously effected very laboriously with the keyboard of the instrument. Exemplary embodiments further permit the transmission of new measuring conditions (for example types of light) very simply by mail of telefax to the user. Similarly, new program versions may be delivered to the user in this manner. Measuring modes, measuring conditions and the like, may be integrated into the operating instructions in the form of bar codes, so that the operator may simply select them and load them into the instrument.

Possible applications of basic features according to the invention are numerous. Equipment configurations (for example from the operating instructions), tables (for example types of light), reference values, calibration values (for example measured values on a calibrating standard) and key sequences (macros) may be entered or printed out. This leads to easier operation in the case of complex functions, the entering of text and numbers or special service functions. Furthermore, new program versions or program extensions may be readily loaded in this manner into the instrument. Finally, it is also possible to secure all of the contents of the memory in this fashion.

BRIEF DESCRIPTION OF THE DRAWINGS

Further advantages and details of the invention will become apparent from the following detailed description of preferred embodiments when read with reference to the drawings, wherein.

DETAILED DESCRIPTION OF PREFERRED EMBODIMENTS

Figure 1:
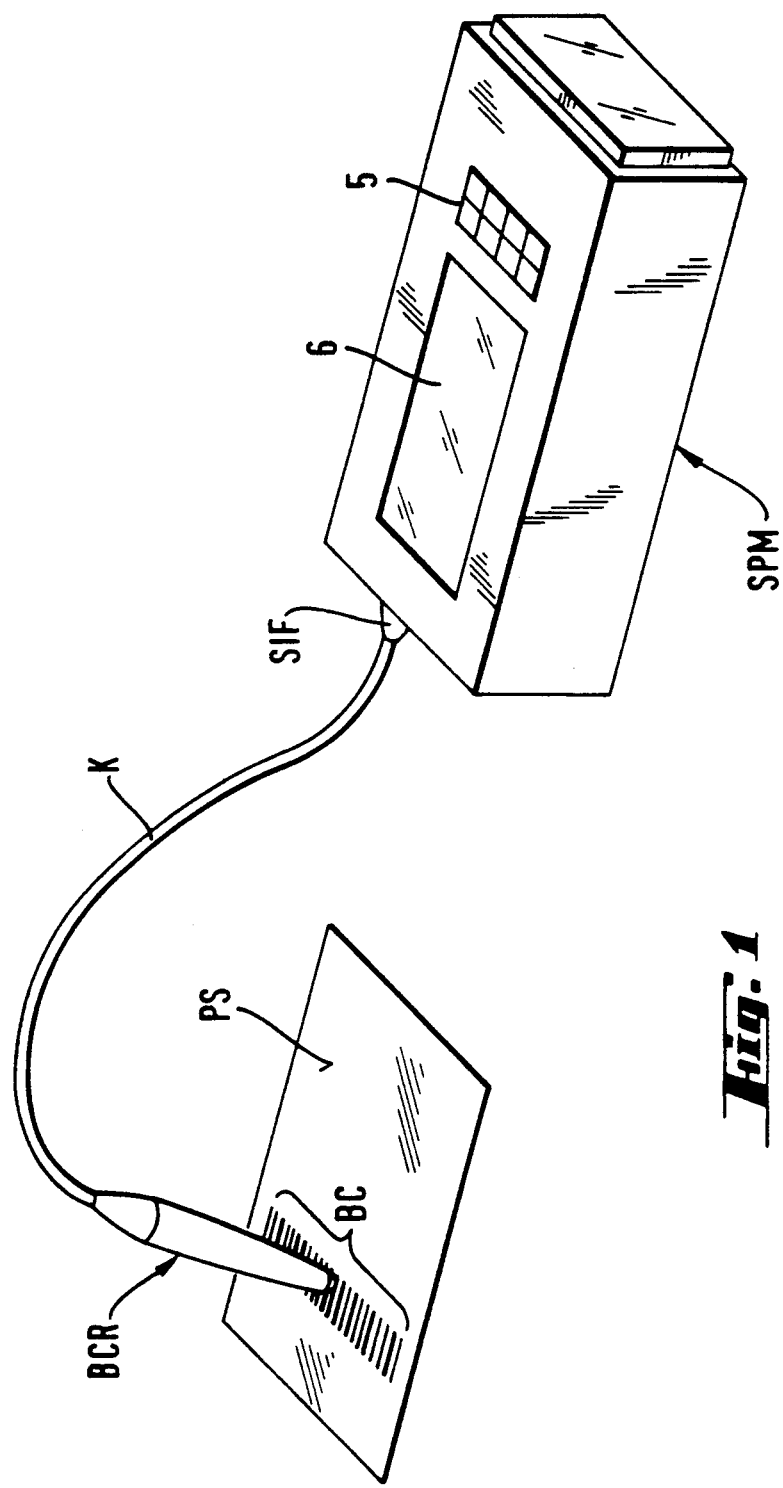
FIG. 1 shows a simplified view of an exemplary spectrophotometer according to the invention.

FIG. 1 shows a basic configuration of a spectrophotometer according to the invention. It comprises the spectrophotometer SPM itself, which is equipped with a serial interface, and a commercial bar code reader (wand) BCR, connected by means of a cable K with an interface connector SIF. The BCR is capable of scanning the BC data printed on a data carrier in the form of a sheet of paper as bar codes.

The spectrophotometer SPM is a commercial, computer controlled instrument. For example, it can be the aforementioned known manual measuring instrument SPM 100 available from Gretag AG. The mechanical and optical configuration of this instrument is described in detail, for example, in U.S. Pat. Nos. 4,968,140, 4,961,646 and 4,929,084, the disclosures of which are hereby incorporated by reference in their entireties. An exemplary fundamental electrical layout is shown in the block diagram of FIG. 2.

Figure 2:
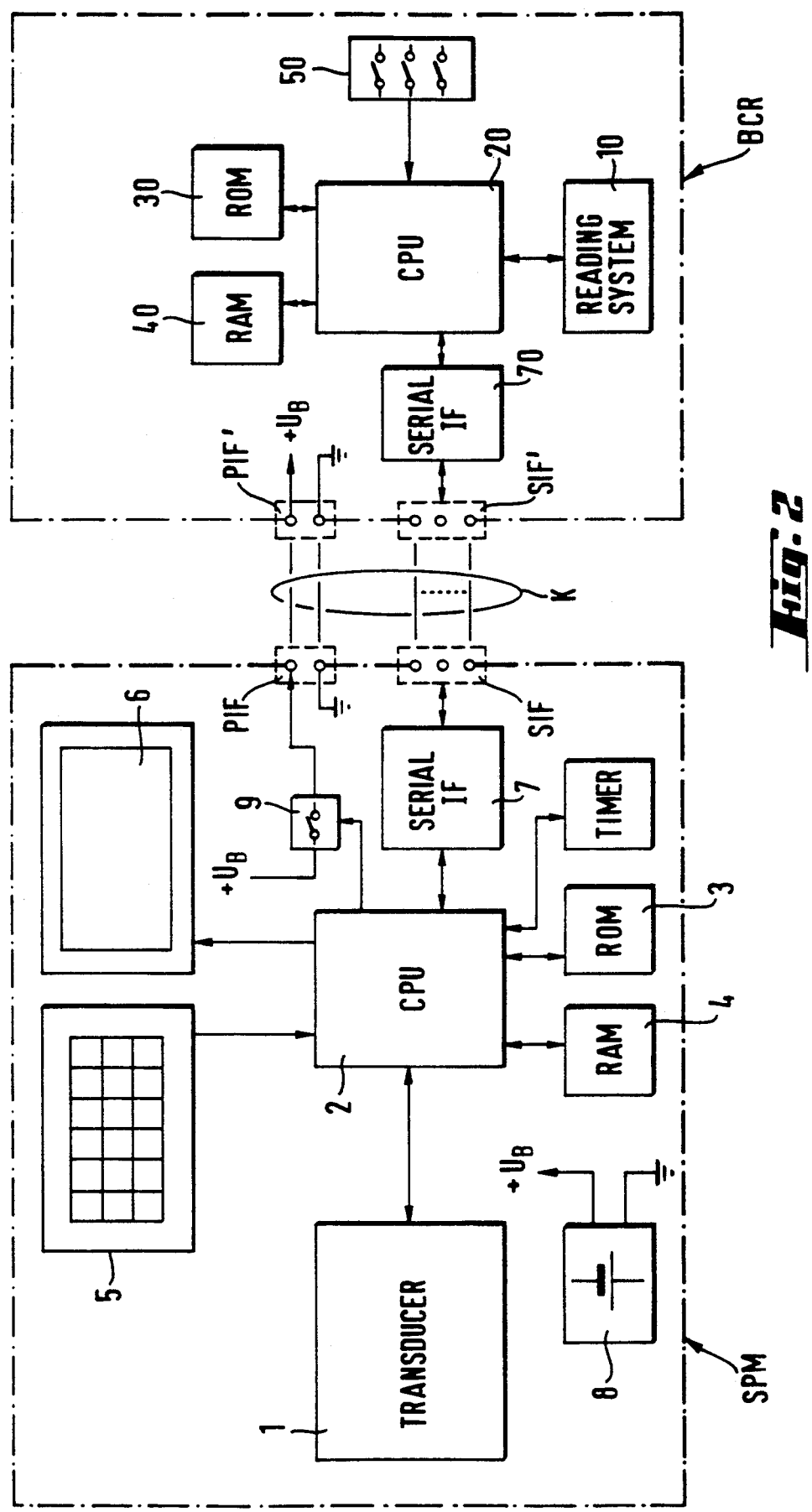
FIG. 2 shows a block diagram of the spectrophotometer of FIG. 1.

As shown in FIG. 2, the SPM instrument comprises a photoelectric measuring transducer 1, which represents the measuring system proper and converts the measuring light originating from the object measured into digital measuring data. It further comprises a computer 2, with a hard disk memory 3 and a working memory 4, which controls the measuring transducer 1 and converts the measured data into measuring results. The computer 1 is equipped with a keyboard 5, an optical display unit 6 for the measuring results and messages of the computer and the aforementioned serial interface 7. A battery 8 supplies the power required. The serial interface 7 leads to the interface plug SIF. Another plug connector PIF conducts, in a manner to be described later, the supply voltage (for example +5 v) from a computer controlled switch 9.

The bar code reader (wand) is of a conventional configuration and comprises a laser based reading system 10, a computer 20, a hard disk memory 30, a working memory 40, a serial interface 70 and several switches to set or program the different functions possible. It is further equipped with an interface plug connector SIF and a supply voltage plug connector PIF, through which it receives the operating voltage from the spectrophotometer SPM. The plug connectors PIF and PIF' and SIF and SIF' are connected with each other, respectively in the operational state by the cable K.

As the bar code reader BCR, for example, the type HBCR-8200 of the Hewlett-Packard Co. may be employed. The configuration and operation of this device is described in readily available manuals for this device, and therefore the device does not require further explanation at this time.

As discussed above, the spectrophotometer is, for example, the aforementioned SPM 100 device of Gretag AG. It is identical with the latter in its configuration and differs only in its programming, to be described later. Another computer controlled color measuring instrument of a comparable nature, equipped with a serial interface for control by means of an external host computer, is described for example in U.S. Pat. No. 4,591,978, the disclosure of which is hereby incorporated by reference in its entirety. No additional detailed explanation of the electrical layout of the spectrophotometer SPM is therefore necessary.

The spectrophotometer SPM is operated by means of the keyboard 5. With the aid of this keyboard the instrument may be turned on and off, its different measuring functions (measuring modes) selected and measuring configurations set. Also, data such as reference and calibration values, etc. may be effected (e.g., input) through an external host computer to be connected to the serial interface SIF. The necessary software is contained in the hard disk memory 30. The software requires no detailed explanation. Furthermore, it is immaterial relative to an understanding of the present invention.

Figure 3:
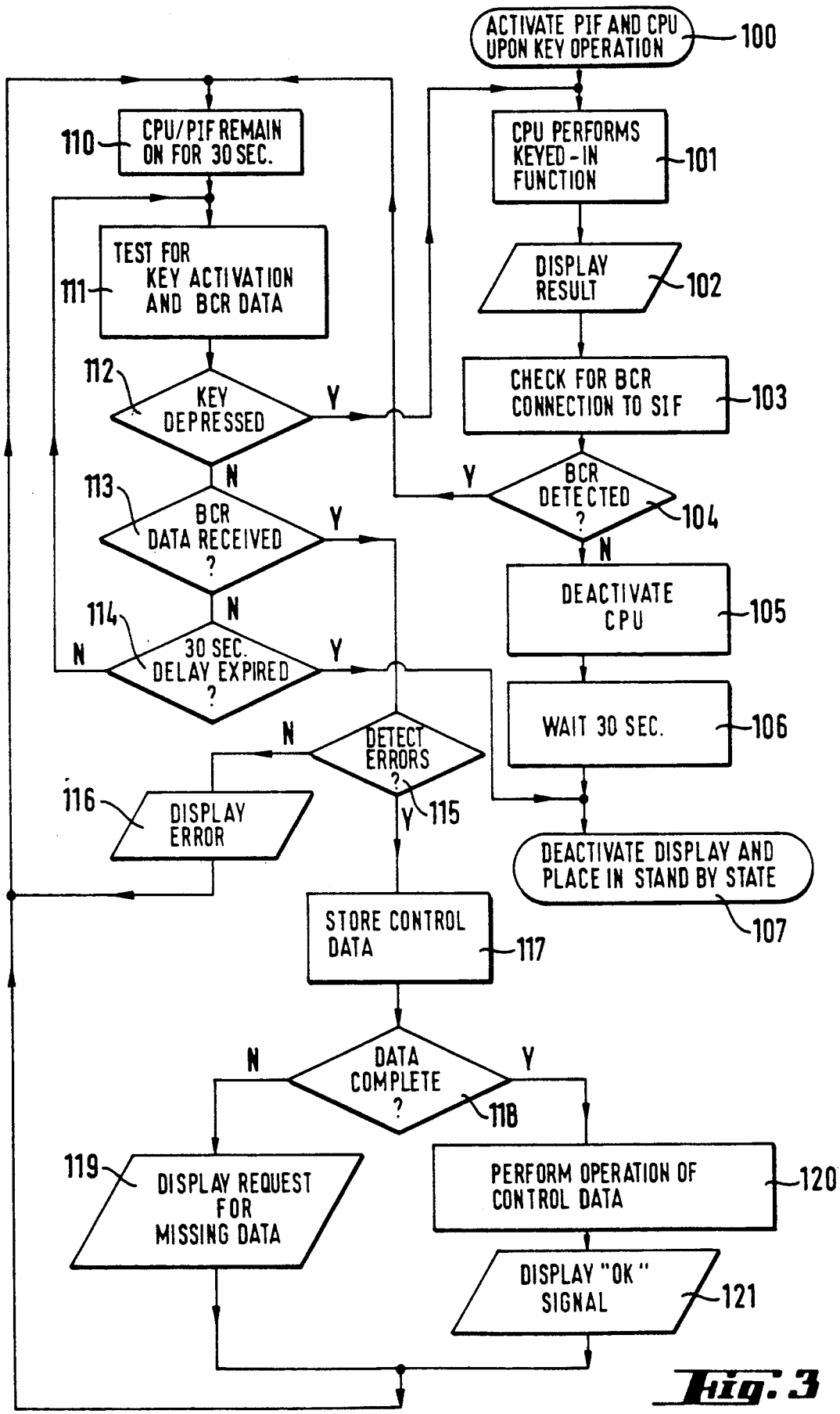
FIG. 3 shows a flow diagram of an exemplary functional segment essential for the invention.
Figure 4:
FIGS. 4-8 show examples of different instructions for the spectrophotometer in the form of bar codes.
Figure 5:
Figure 6:
Figure 7:
Figure 8:
Figure 8:
Figure 8:
Figure 8:
Figure 8:
Figure 8:
Figure 8:
Figure 8:
Figure 8:
Figure 8:

As mentioned above, the manual operation of the spectrophotometer SPM by means of its limited keyboard requires in some cases complex key sequences, in particular if larger volumes of data, for example in the initial programming of specific light type data, are to be entered. To facilitate and simplify the operation, the operation of the instrument is extended by another possibility according to a basic feature of the invention, by programming the computer 2 so that it may be addressed as the operating element not only by the keyboard 5 or an external host computer connected with the serial interface SIF, but additionally also by a reader device connected with the interface SIF (e.g., the bar code reader BCR). The computer 2 detects whether the reader is connected with the interface and receives and interprets the data supplied to it by the reader and carries out the operations corresponding to the control data received, as if it had received the commands from the host computer or the keyboard. The necessary functional processes, which are additional to the known devices, (for example the SPM 100 of Gretag AG), are shown in the flow diagram of FIG. 3.

In a preferred exemplary embodiment shown, the control data for the computer which is used to replace the corresponding keyboard operations, are present as bar codes on paper or the like, and consequently, the reader device is a bar code reader. However, the invention is not restricted to this. The control data may also be recorded in any other machine readable form on any other type of data carrier, in which case a conventional reading device used in computer technology may be employed, whereupon the reading device would, for example, be a magnetic tape reader or a diskette drive. It is merely necessary that the reader be able to transfer the recorded control data in a digital form in keeping with a predetermined protocol through the interface to the computer 2 of the spectrophotometer.

The spectrophotometer SPM is equipped, exactly as the known instrument SPM 100 of Gretag AG, with an automatic power saving device in order to preserve the built in battery. Normally, the computer 2 and the other major power consumers are turned off or are in a stand-by mode. Upon the actuation of a key the computer 2 is briefly activated, for example for about two seconds, performs the operation desired and displays the result on the display means 6. It is then deactivated, while the display is discontinued after a certain delay only. However, if the computer 2 is deactivated, the voltage supply connection PIF is also deactivated by means of the switch 9 actuated by the computer and the bar code reader is without power. In the operation of the bar code reader according to the invention another functional process is therefore necessary, which is explained hereinbelow with reference to the flow diagram in FIG. 3.

Starting from the stand-by state, the computer and thus the power supply connection PIF are activated by operating any key of the keyboard (box 100), whereupon the computer performs the action corresponding to the key used (box 101) and displays the result on the display device 6 (box 102). The computer 2 next ascertains whether the bar code reader BCR (or another suitable reader) is connected with the interface connector SIF (boxes 103 and 104). This may be effected for example in conventional manner by sending a predetermined signal to the bar code reader, which then responds with a preset message. If the computer receives the message, the reader is connected, otherwise it is not. If no bar code reader BCR is connected, the computer 2 is deactivated (box 105), followed by a waiting period of for example 30 seconds (box 106), after which the display 6 is also turned off (box 107) and the instrument returned to the initial stand-by state. With the exception of the testing of the bar code reader (boxes 103 and 104), the process is the same as with the known spectrophotometer SPM 100 of Gretag AG.

If the computer 2 recognizes a connected bar code reader BCR (box 104), initially a time window of for example 30 seconds is opened, during which the computer 2 and the power supply connection PIF remain activated (box 110). A test (box 111) is now performed to determine whether a key of the keyboard 6 had been depressed (box 112) or whether control data had been received from the bar code reader BCR (box 113). If none of these is true, it is determined (box 114) whether the time window had been closed, i.e., the delay time has expired. If the latter is the case, the computer 2 and the display 6 are deactivated (box 107). The instrument is then again in the stand-by state.

If during the open time window a key is depressed, the program branches to box 101, performs the action corresponding to said key, displays the result (box 102) and repeats the test to ascertain whether there is a connection of the bar code reader (boxes 103 and 104). If the reader BCR is connected, the program jumps to box 110 and the time window is reopened.

If during the open period of the time window control data is received from the bar code reader BCR (box 113), this data is tested for errors (box 115). This may be effected, for example, in a conventional manner by an error recognition code transmitted by the bar code reader BCR according to predetermined, conventional standards. If a reading or transmission error is detected (box 115), an appropriate error signal is sent to the display device 6 (box 116) and the program loop is repeated with the resetting of the time window (box 110). If the control data are free of errors, they are stored in the working memory 4 (box 117) and then tested for completeness (box 118). If they are not yet complete, a request for the entry of the missing parts of the control data is transmitted to the display device 6 (box 119) and the program loop repeated together with the resetting of the time window (box 110). If the control data are complete, the action corresponding to their significance is carried out (box 120) and an OK signal sent to the display 6 (box 121). The action defined by the control data is carried out analogously to an action due to control data introduced by means of an external host computer and thus does not require any detailed explanation. Following the OK signal, the program loop is again repeated beginning with the reopening of the time window (box 110) and so on. If no control data are received from the bar code reader BCR or no key is depressed, the time window is closed upon the expiration of its period (box 114) and the instrument is returned to its stand-by state (box 107).

As the bar code, a standard code may be used, such as described for example in the manual for the bar code reader HBCR-8200 by Hewlett-Packard. Each code strip contains a defined start signal, the information, a check sum and defined stop signals. By means of the check sum, the bar code reader is able to automatically recognize whether the code strip had been read correctly and to send a corresponding signal to the computer. These functions are implemented in a standardized manner in commercial bar code readers (wands).

As the length of a code strip is limited by standards (for example, the information may contain a maximum of 31 symbols) and the control data to be transmitted to the computer frequently comprise a longer set of data, the data must often be divided into several data sets. Each partial data set contains information concerning the number of partial data sets belonging to the complete set, its position within the complete data set (position number) and finally the part of the signal itself. The entirety of the signal parts then reproduces the complete control data. If the control data include only one partial data set, obviously the information concerning the number and position number of partial data sets may be omitted.

FIGS. 4–7 show examples of control data in the form of bar codes, which actuate the functions "actuate instrument permanently", "trigger signal", "set parameters" and "reset display" in the spectrophotometer SPM.

FIGS. 8a–8j exhibit an example of control data, effecting the loading of an entire table of light type data into the spectrophotometer SPM. The control data are present in the form of 10 individual bar code strips, each containing a part of the control data, together with the aforementioned start and stop signals and the total number of strips and their position number.

The transfer process is as follows:

With the bar code reader BCR, the individual code strips are read in an arbitrary sequence and transferred to the computer. The latter recognizes from the cotransmitted codes for the number of partial signals and the position numbers, the individual parts of the control data. It stores them and issues request signals for the reading in of missing or erroneous parts and acknowledges each successful and correct entry operation acoustically. When all parts of the control data have been read in correctly, this is displayed optically and/or acoustically.

Another important aspect of the present invention is that the computer may also be programmed to output the data stored therein to a memory device connected with its interface, for storage on a recording medium. It is especially convenient to print out the data that is of interest using a printer with graphic capabilities in the form of bar codes. These can later be read in by means of the bar code reader in order, for example, to retrieve an earliest configuration in a simple manner. The conversion of the data into bar codes is carried out, for example, according to the guide lines of the aforementioned Hewlett-Packard manual for the HBCR-8200 and analogously to the above discussion. It is possible in this manner to secure the entire program of the computer, i.e., the complete contents of its memory in the form of bar codes, or the like.

It will be appreciated by those of ordinary skill in the art that the present invention can be embodied in other specific forms without departing from the spirit or essential character thereof. The presently disclosed embodiments are therefore considered in all respects to be illustrative and not restrictive. The scope of the invention is indicated by the appended claims rather than the foregoing description and all changes which come within the meaning and range of equivalents thereof are intended to be embraced therein.

What is claimed is:

1. Photometric system using a computer controlled photoelectric measuring instrument, said system comprising:
    a photoelectric measuring transducer for converting measuring light into digital measured data;
    a digital computer for controlling the measuring transducer and processing the measured data into measuring results;
    an operating keyboard for controlling measuring functions of the measuring transducer and the digital computer, for entering data into the computer, and for causing said digital computer to open a time window during which said digital computer is placed into a state for receiving control data transmitted by an external reading device;
    an optical display device for displaying measured results and messages of the computer; and an interface for connecting said external reading device to the computer, said external reading device being connected with the interface for reading and transferring control data to the computer such that said computer is controlled in response to the keyboard and in response to control data introduced through the interface, said control data being recorded in a machine readable form of an external data carrier read by the reading device.

2. Photographic system according to claim 1, wherein said external reading device includes:

a bar code reader, and the control data are recorded as a bar code and read and transferred to the computer by the bar code reader.

3. Photographic system according claim 2, wherein said control data includes configurations of the measuring instrument, measuring functions or modes, measuring conditions, reference and calibration values, and program data for transfer to the computer.

4. Photometric process using a computer controlled photoelectric measuring instrument, said process comprising the steps of:

photoelectrically measuring and converting measuring light into digital measured data;

controlling the measuring and processing of the measured data into measuring results with a computer;

controlling the measuring functions by operating a keyboard to enter data into the computer and to open a time window during which said computer is placed into a state for receiving control data transmitted by an external peripheral apparatus;

connecting said external peripheral apparatus to an interface of the computer; and externally reading and transferring control data to the computer via the interface such that said computer is controlled in response to the keyboard and in response to control data introduced through the interface, said control data being recorded in a machine readable form on an external data carrier which is read during said step of externally reading.

5. Process according to claim 4, wherein the step of externally reading and transferring further includes recording control data as a bar code which is read and transferred to the computer by a bar code reader, said process further including a step of:

optically displaying measured results and messages of the computer.

6. Process according claim 5, wherein said control data includes configurations of the measuring instrument, measuring functions or modes, measuring conditions, reference and calibration values, and program data for transfer to the computer.

7. Process according to claim 6, wherein the control data transferred to the computer are tested for errors and for completeness, and corresponding error and completeness messages are displayed.

8. Process according to claim 7, wherein the bar code reader is activated only during the duration of the time window.

9. Process according to claim 8, wherein the control data are provided with an error detection code for testing the control data.

10. Process according to claim 9, further including a step of storing control data as a plurality of partial data sets, with each partial data set containing information concerning a total number of partial data sets belonging to a complete set of data and a position of each partial data set within the complete data set.

11. Process according to claim 10, wherein data stored in the computer is output through the interface to an external data carrier and recorded in a machine readable form.

12. Process according to claim 11, wherein data stored in the computer is recorded as a bar code by a printer with graphic capabilities.

13. Computer controlled spectrophotometer, comprising:

a photoelectric measuring transducer for converting measuring light into digital measuring data;

a digital computer for controlling said measuring transducer and for processing the measuring data into measured results;

an operating keyboard for controlling measuring functions of the measuring transducer and the digital computer and for entering data into the computer to open a time window;

an optical display device for displaying the measured results and messages of the computer including a message which indicates when erroneous or incomplete digital data are detected by the computer;

a bidirectional interface for connecting an external peripheral apparatus to the computer; and a code reader connected as said external peripheral apparatus to the computer via said interface, said computer further including:

a working memory for storage of digital data received from the code reader, said computer being provided for opening said time window in response to actuation of the keyboard and determining within the time window whether the code reader is connected with the interface, said computer further being provided for receiving digital data produced by the code reader via the interface, for testing the digital data received for errors and completeness, for carrying out an appropriate action by interpreting complete digital data free of errors, and for closing the time window.

14. Photometer according to claim 13, further comprising:

a power voltage connector for the code reader, the computer supplying power to the power voltage connector only if the time window is open.

15. Photometer according to claim 14, further comprising:

an interface for connection to a printer, said computer outputting configuration data, measuring function data, measuring condition data, reference and calibration value data, and program data to the printer.

16. Photometer according to claim 15, wherein the computer controls the printer to print output data in a bar code form readable by the code reader.

* * * * *